(12) United States Patent
Angelescu et al.

(10) Patent No.: US 7,784,330 B2
(45) Date of Patent: Aug. 31, 2010

(54) VISCOSITY MEASUREMENT

(75) Inventors: Dan E. Angelescu, Cambridge, MA (US); Hua Chen, Cambridge, MA (US); Christopher Harrison, Auburndale, MA (US); Matthew Sullivan, Belmont, MA (US); Jacques Jundt, Newton Highlands, MA (US)

(73) Assignee: Schlumberger Technology Corporation, Cambridge, MA (US)

( * ) Notice: Subject to any disclaimer, the term of this patent is extended or adjusted under 35 U.S.C. 154(b) by 211 days.

(21) Appl. No.: 11/973,218

(22) Filed: Oct. 5, 2007

(65) Prior Publication Data

US 2009/0090172 A1    Apr. 9, 2009

(51) Int. Cl.
G01N 11/08    (2006.01)
(52) U.S. Cl. ..................................... 73/54.09
(58) Field of Classification Search ................. 73/54.09
See application file for complete search history.

(56) References Cited

U.S. PATENT DOCUMENTS

| | | | |
|---|---|---|---|
| 5,511,416 A | 4/1996 | Shambayati | |
| 6,681,616 B2* | 1/2004 | Spaid et al. | 73/54.07 |
| 6,843,121 B1* | 1/2005 | DeBar et al. | 73/202 |
| 6,915,679 B2* | 7/2005 | Chien et al. | 73/54.01 |
| 6,990,851 B2* | 1/2006 | Spaid et al. | 73/54.13 |
| 7,081,615 B2 | 7/2006 | Betancourt et al. | |
| 7,162,927 B1 | 1/2007 | Selvan et al. | |
| 7,194,902 B1 | 3/2007 | Goodwin et al. | |
| 2002/0022261 A1* | 2/2002 | Anderson et al. | 435/287.2 |
| 2002/0077759 A1 | 6/2002 | Cohen et al. | |
| 2002/0166367 A1 | 11/2002 | Bures | |
| 2003/0041652 A1 | 3/2003 | Spaid et al. | |
| 2005/0183496 A1 | 8/2005 | Baek | |

(Continued)

FOREIGN PATENT DOCUMENTS

WO    01/86254 A2    11/2001

(Continued)

OTHER PUBLICATIONS

Wu et al., MEMS Flow Sensors for Nanofluidic Applications, Sensors and Actuators A 89, 2001, pp. 152-158.*

(Continued)

*Primary Examiner*—Hezron Williams
*Assistant Examiner*—Rodney T Frank
(74) *Attorney, Agent, or Firm*—James McAleenan; Vincent Loccisano; Brigid Laffey

(57) ABSTRACT

A micro-fluidic device and methods for measuring one or more rheologic properties of a fluid. The micro-fluidic device includes a substrate and at least one cover bonded to a surface of the substrate with a fluid channel formed in at least one of the cover or the substrate. Further, the micro-fluidic device includes a first differential pressure gauge that can have a first differential pressure sensor in fluid communication with both a first pressure site and a second pressure site. Further still, the micro-fluidic device includes the first pressure site and the second pressure site that can be spaced apart by a first section of the fluid channel. Also, the micro-fluidic device includes a data processor communicatively coupled to the first differential pressure sensor, so as to receive data generated by the first differential pressure sensor.

25 Claims, 7 Drawing Sheets

U.S. PATENT DOCUMENTS

| | | | |
|---|---|---|---|
| 2005/0202504 A1* | 9/2005 | Anderson et al. | 435/6 |
| 2005/0263281 A1 | 12/2005 | Lovell et al. | |
| 2006/0008382 A1 | 1/2006 | Salamitou et al. | |
| 2006/0008913 A1 | 1/2006 | Angelescu et al. | |
| 2006/0094694 A1 | 5/2006 | Owada et al. | |
| 2006/0179923 A1 | 8/2006 | Burns et al. | |
| 2006/0246490 A1* | 11/2006 | Anderson et al. | 435/6 |
| 2007/0061093 A1 | 3/2007 | Angelescu et al. | |
| 2007/0077038 A1 | 4/2007 | Wall et al. | |
| 2007/0289739 A1 | 12/2007 | Cooper et al. | |

FOREIGN PATENT DOCUMENTS

| | | | |
|---|---|---|---|
| WO | 2006094694 A1 | 9/2006 | |
| WO | 2007077038 A1 | 7/2007 | |

OTHER PUBLICATIONS

Harrison et al., Vibrating Wire Viscosity Sensor, U.S. Appl. No. 11/937,035, filed Nov. 8, 2007.

Harrison et al., Microfluidic Downhole Density and Viscosity Sensor, U.S. Appl. No. 11/937,078, filed Nov. 8, 2007.

Benes et al., Viscosity Sensor Based on a Symmetric Dual Quartz Thickness Shear Resonator, Proceedings of the 2003 IEEE International Frequency Control Symposium and PDA Exhibitiion, pp. 1048-1054.

Fann Instrument Company, http://www.fann.com/product_overview1.asp?iprod=37869&catid=4, accessed Jun. 16, 2008, p. 1.

Endress+Hauser, Coriolis Mass Flowmeters, http://www.us.endress.com/eh/sc/america/us/en/home.nsf/?Open&DirectURL=DBEE99C25AE98A58C1256DCD005C6FAB, Accessed Jun. 16, 2008, pp. 1-3.

Alicat Scientific, Liquid Flow Meters, http://www.alicatscientific.com/products/liquid_flow_meter.php, Accessed Jun. 16, 2008, pp. 1-2.

Whorlow, Rheological Techniques, 2nd Edition, Ellis Horwood Limited, England, 1992, pp. 43-68.

Cannon Instrument Company, Viscosity & Flash Point Standards, 2007, pp. 1-8.

Son, Determination of Shear Viscosity and Shear Rate from Pressure Drop and Flow Rate Relationship in a Rectangular Channel, Polymer, 2007, vol. 48, pp. 632-637.

Patent Cooperation Treaty International Search Report, Form PCT/ISA/210, Date of mailing Feb. 4, 2009, pp. 1-4.

* cited by examiner

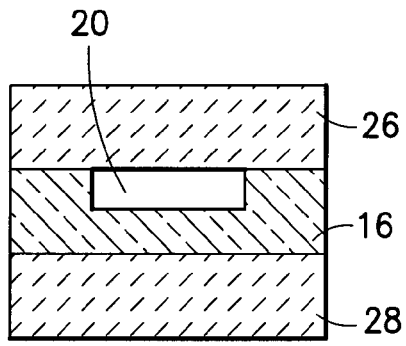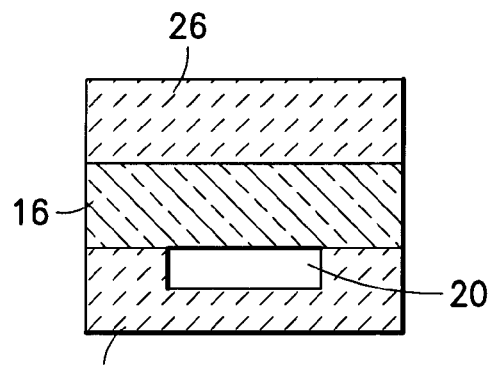
FIG.2A  FIG.2B
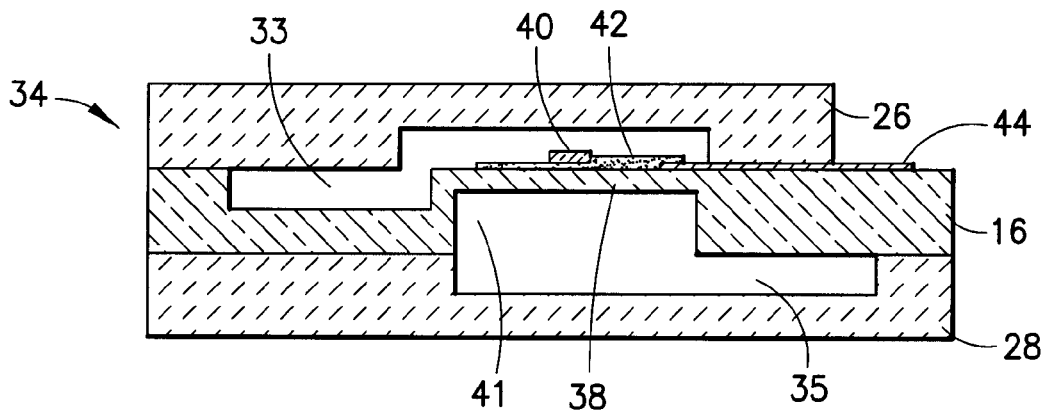
FIG.3
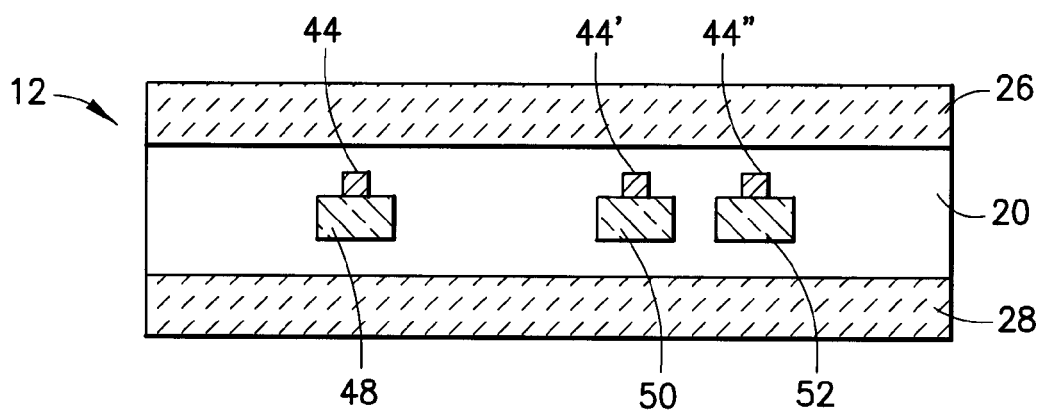
FIG.5

VISCOSITY MEASUREMENT

BACKGROUND OF THE INVENTION

1. Field of the Invention

The invention relates to a device and methods to determine rheological properties of a fluid, such as absolute viscosity. More particularly, the fluid flows through a micro-fluidic sensor, e.g., micro-fluidic device. A Micro Electro Mechanical System (MEMS) device that is a component of the micro-fluidic sensor measures a pressure drop and, optionally, a flow rate. Utilizing this data, a processor can calculate rheological properties.

2. Description of the Related Art

Fluid analysis is important in the oil field industry. Construction decisions for a new well are largely based on measurements of fluid properties, as performed down hole (directly on reservoir fluids) or up hole (on the surface). Information regarding the chemical composition, phase diagram, density and viscosity of the fluid are critical to deciding which zones of a particular well are economical to produce and to installing the right infrastructure for that zone. Other industries are also interested in monitoring various parameters of a fluid, such as viscosity, to assure, for example, proper lubrication of certain parts or to control fabrication processes.

Viscosity is the internal resistance to shear or flow exhibited by a fluid and is a measure of the adhesive/cohesive or frictional fluid property. The resistance is caused by intermolecular friction exerted when layers of fluids attempt to slide by one another. "Apparent viscosity" is frequently used for quality control purposes. The viscosity of a test fluid is compared to the viscosity of a control fluid in a common piece of equipment, for example, the torque necessary to rotate a spindle in the fluid may be compared. However, the measurements only have meaning for the specific test equipment and over a narrow range of viscosities.

"Absolute viscosity" is the tangential force per unit area required to move one horizontal plane with respect to another at unit velocity when maintained a unit distance apart by the fluid. This can be expressed mathematically by the formula:

$$\eta = \tau_w / \dot{\gamma} \quad (1)$$

where $\eta$ is the viscosity, $\tau_W$ is the shear stress applied at one of the horizontal planes and $\dot{\gamma}$ is the shear rate of the fluid at the same plane. Absolute viscosity, while more difficult to measure, provides a more meaningful result and is independent of test equipment and method. Kinematic viscosity is a derived quantity which can be obtained by dividing the absolute viscosity of a fluid by its mass density. In some instances, sensors may directly measure the kinematic viscosity, such as the tortional plumb bob viscometer, "Viscolite" sold by Hydramotion Ltd of York, England.

Fluid flow may by "Newtonian" or "non-Newtonian." A fluid is Newtonian if the viscous stress tensor is linearly proportional to the shear rate tensor, with viscosity being the constant of proportionality. A fluid is non-Newtonian otherwise, due to either viscosity that is not constant with shear rate, normal stress differences, or some combination of both effects.

For an incompressible Newtonian fluid flowing in the fully developed laminar regime through a tube of circular cross-section with radius R, the shear stress, $\tau_W$, and apparent shear rate, $\dot{\gamma}_A$, at the wall of the tube can be simply related to the pressure drop, $\Delta p$ that develops along the tube of length, L, and respectively the volumetric flow rate, Q, by the following formulae (see reference: Rheological Techniques, $2^{nd}$ edition, R. W. Whorlow):

$$\tau_w = R\Delta p/2L \quad (2)$$

$$\dot{\gamma}_A = 4Q/\pi R^3 \quad (3)$$

The above definition for the wall shear stress is true for both Newtonian and non-Newtonian fluids flowing in a tube with circular symmetry in the fully developed laminar regime. The shear rate above is referred to as the apparent shear rate, as it is equal to the actual shear rate only in the case of a Newtonian fluid. These formulae, when used in conjunction with Equation (1) above, lead to an expression which relates the viscosity, $\eta$, to these same quantities:

$$\eta = \frac{\pi R^4 \Delta p}{8QL} \quad (4)$$

In the case of a non-circular cross-section of the tube, the numerical factor in the denominator is different from the value 8 shown above, and can be obtained either analytically for some geometries, by a numerical calculation for arbitrary geometries, or experimentally by calibration using known viscosity standards. This will be discussed in more detail in a subsequent section. Immediately below is a discussion of the appropriate interpretation to measure the viscosity of a non-Newtonian fluid with a capillary viscometer with circular cross-section.

For an incompressible non-Newtonian fluid flowing in a cylindrical tube, the shear rate at the wall is more difficult to derive as the shear rate given in Eq. 3 above is no longer exact, and needs to be calculated using the Rabinowitsch equation (same reference: Rheological Techniques, $2^{nd}$ edition, R. W. Whorlow):

$$\dot{\gamma}_W = \frac{3n+1}{4n} \dot{\gamma}_A \quad (5)$$

where n is defined as $$n = \frac{\partial(\log \Delta P)}{\partial(\log Q)} = \frac{\partial(\ln \tau_W)}{\partial(\ln \dot{\gamma}_A)} \quad (6)$$

$\dot{\gamma}_W$ is the actual shear rate at the wall and $\dot{\gamma}_A$ is the shear rate ($4Q/\pi R^3$) that would be present if the fluid were Newtonian. $\tau_W$ is the shear stress at the wall and is given by $R\Delta p/(2L)$. Since this expression involves a derivative, the actual wall stress can only be determined if several ($\Delta p$, Q) value pairs are known and more robustly if several pairs are known. The shear rate dependent viscosity can then be calculated for a non-Newtonian fluid as:

$$\eta = \frac{4n}{3n+1} \frac{\pi R^4 \Delta p}{8QL} \quad (7)$$

As mentioned earlier, a viscosity measurement of Newtonian fluid in a non-circular geometry requires a different analysis due to its lower degree of symmetry. A simple example would be that of a slit die where one of the lateral sizes is much larger than the other by a factor of 10 or larger, allowing one to simply treat the system as one-dimensional.

This would apply in a capillary that was very shallow and very wide, both lateral dimensions being small compared to its length. In this case the shear stress at the wall is:

$$\tau_W = \frac{H}{2}\frac{\Delta P}{L} \quad (8)$$

where H is the channel depth. Furthermore, the apparent shear rate for a Newtonian fluid is:

$$\dot{\gamma}_A = \frac{6Q}{WH^2} \quad (9)$$

where W is the channel width. The viscosity is then calculated as:

$$\eta = \frac{WH^3 \Delta p}{12QL} \quad (10)$$

Once again, for a non-Newtonian fluid, a slightly more complicated analysis is necessary, which gives rise to the following shear rate at the wall surface:

$$\dot{\gamma}_W = \frac{2n+1}{3n}\dot{\gamma}_A \quad (11)$$

The viscosity calculation for a slit geometry is appropriately modified for non-Newtonian fluids as:

$$\eta = \frac{3n}{2n+1}\frac{WH^3 \Delta p}{12QL} \quad (12)$$

where once again n is defined by formula (6) above.

The result for the slit die can be generalized, in certain cases, to a rectangular die where the two lateral dimensions (H and W) are comparable. In this case the shear stress at the wall is:

$$\tau_W = \left(\frac{\Delta PH}{2L}\right)\frac{1}{H/W+1} \quad (13)$$

For a Newtonian fluid, an analytical solution for the viscosity can be derived for all combinations of H and W:

$$\eta = \frac{\Delta p H^3 W^3}{12QL(H+W)^2 f^*\left(\frac{H}{W}\right)} \quad (14)$$

where the function $f^*(x)$ is defined as:

$$f*(x) = \left[\left(1+\frac{1}{x}\right)^2\left(1 - \frac{192}{\pi^5 x}\sum_{i=1,3,5,...}^{\infty}\frac{\tanh\left(\frac{\pi}{2}ix\right)}{i^5}\right)\frac{WH^2}{6Q}\right] \quad (15)$$

and is given in the Table that follows (from Son, Polymer 48, p. 632, 2007).

TABLE 1

| H/W | f* |
|---|---|
| 0.00 | 1.0000 |
| 0.05 | 0.9365 |
| 0.10 | 0.8820 |
| 0.15 | 0.8351 |
| 0.20 | 0.7946 |
| 0.25 | 0.7597 |
| 0.30 | 0.7297 |
| 0.35 | 0.7040 |
| 0.40 | 0.6820 |
| 0.45 | 0.6634 |
| 0.50 | 0.6478 |
| 0.55 | 0.6348 |
| 0.60 | 0.6242 |
| 0.65 | 0.6155 |
| 0.70 | 0.6085 |
| 0.75 | 0.6032 |
| 0.80 | 0.5991 |
| 0.85 | 0.5961 |
| 0.90 | 0.5942 |
| 0.95 | 0.5931 |
| 1.00 | 0.5928 |

For non-Newtonian fluids in a rectangular geometry, there is no analytical solution, though numerical solutions have been tabulated for several ratios of H/W. Reference is once more made to Son, Polymer 48, p. 632, 2007, where the tabulation of many such solutions and the calculation algorithm Son provides enable the viscosity of non-Newtonian fluids to be measured in a geometry of rectangular dimensions.

Many methods to measure apparent or actual viscosity are available for laboratory or industrial use. A simple method is by measuring the time required for a volume of fluid to flow out an outlet with a well defined geometry, such as a Marsh funnel. Alternatively, a shear strain can be applied to a fluid by confining it between two rotating surfaces, such as two flat plates, two concentric cylinders, or a cone and a plate, while measuring the sheer stress developed. As another alternative, stress on a rotating object immersed in a fluid may be monitored. The ratio of stress to strain, normalized by the specific device geometry, provides a direct measurement of absolute viscosity. This is the principle operation of many commercial laboratory devices.

Further, flow through a pipe generates a pressure drop which can be monitored using differential pressure gauges. The flow itself is either imposed externally, such as by a volumetric pump, or monitored using various types of flow metering devices. If the flow is laminar and the fluid is Newtonian, then knowledge of the volumetric flow rate, pipe geometry and pressure drop across the pipe provides enough information to determine the viscosity of the flowing fluid. This principle is used in some commercial viscosity meters where mass flow rate is obtained, for example, from a Coriolis type flow meter. In this case, the resulting quantity is a kinematic viscosity and the absolute viscosity can be obtained only if the density is known independently.

Alternatively, the flow rate can be imposed and pressure sensors used to monitor pressure drop. By imposing several flow rates and measuring the corresponding pressure drops, some non-Newtonian aspects of the fluid can be observed. Such principles have also been applied within micro-fluidic devices. For example, the expression "Micro-fluidic" can refer to a sensor where fluid is forced into sub-millimeter channels. Typically, these channels have a diameter of from one to a few hundred microns. It should be noted that sometimes the same physical principles are used to determine another parameter, such as fluid flow rate while assuming a known viscosity. As a laminar character of the flow is important in this kind of measurement, methods have been devised to transform a flow that may be turbulent into several laminar substreams by using one or several bypasses. Thermal methods are commonly used to measuring flow rate, of particular prominence being hot wire anemometry methods.

Published U.S. Patent Application, Publication No. US 2005/0183496 A1, to Baek discloses a micro-fluidic rheometer formed from three etched layers. A cavity formed in the top layer is bonded over a mid-layer to form a channel. A bottom side of the mid-layer includes one-half of a pressure transducer in the form of a capacitor. A bottom piece has the other half of the transducer (other capacitor plate) and electrical connections, resulting in an absolute pressure gauge. Deflection of the bottom side of the channel changes the spacing between the two plates changing the electrical parameters of the capacitor. Several such absolute pressure gauges are placed along a fluidic channel in the shape of a slit. A pump is used to introduce a test liquid and the pump and or a valving system is used to control the flow rate.

The resonance curve shape of a resonator immersed in a fluid can be used to infer viscosity, and in some cases, the density of the fluid. The resonance device can be driven by mechanical, electromagnetic or piezoelectric methods, while the oscillation amplitude can be detected using the device as a transducer, using external gauges to measure strain, or using optical (e.g. interferometry) means to perform a direct measurement. Examples of vibrating sensor are disclosed in WO 2006/094694 A1 and WO 2007/077038 A1, both titled "A Density and Viscosity Sensor" and both by Schlumberger Technology B.V.

As another example of viscosity measurement metrology using a vibrating object, U.S. Pat. No. 7,194,902 to Goodwin, et al. discloses a down hole viscosity measuring system for oil wells. This system includes a tension wire that extends through a moving fluid. The quality factor of the resonance curve is a function of absolute viscosity.

U.S. Patent Publication No. US 2007/0061093 A1 to Angelescu, et al. discloses a method and apparatus to measure the flow rate of a fluid in a fluid channel. A flowing fluid first passes an injection element that injects a tracer into the fluid flow. This tracer is subsequently detected by first and second downstream sensors. Data from the injection element and the detection sensors are communicated to a processor that utilizes the time data to determine flow rate.

U.S. Pat. No. 7,194,902 and published Patent Application Nos. US2005/0183496 A1 and US2007/0061093 A1 are all incorporated by reference in their entireties herein.

While the above systems determine certain features of a fluid, such as viscosity or flow rate, or are effective to determine absolute viscosity under controlled parameters, there remains a need for a micro-fluidic system effective to determine absolute viscosity accurately, potentially at high ambient pressure, and potentially without prior knowledge of flow rate.

SUMMARY OF THE INVENTION

The present invention relates to a micro-fluidic device, e.g., sensor, for measuring one or more rheologic properties of a fluid. In a preferred embodiment, the micro-fluidic device includes a first substrate in which a differential pressure gauge is formed having one side in fluid communication with a first pressure site, and the other side in communication with a second pressure site, the two pressure sites being connected by a fluid channel. The fluid channel may be made in the same substrate as the differential pressure gauge, or it may be made in a different substrate, adjacent and bonded to the first substrate. A signal conduit effectively transmits data generated by the first differential pressure sensor to a data processor. In a second embodiment, the micro-fluidic device includes, in addition to the above, a flow measurement device which allows the flow rate of the fluid flowing through the channel to be determined. The flow measurement device may be built in the same substrate as the differential pressure gauge. A third embodiment incorporates a fluid channel, a flow measurement device, and one or more absolute pressure sensors in communication with one or more locations along the fluid channel. The differential pressure sensor, absolute pressure sensors, and the flow rate sensors referred to above may be MEMS devices.

According to another aspect of the invention, an application of the micro-fluidic sensor may be for the oil services industry where determining the rheological properties of a fluid is necessary. A rheological property, viscosity, may be calculated for a fluid having Newtonian flow if the flow rate and the pressure drop are known. For some applications where the fluid may be delivered to the sensor by an external flow regulating device, such as in a lab setting or in an up hole setting, the sensor may be utilized as described in the preferred embodiment of the preceding paragraph. For applications where flow cannot be externally controlled, as may be the case in a down hole environment, the second or third embodiments of the preceding paragraph may be preferred.

According to another aspect of the invention, when determining rheological properties of fluids having non-Newtonian flow, data obtained from multiple differential pressure gauges distributed across multiple flow channels, may be formed on the same or on adjacent substrates, and can be measured to obtain the viscosity as a function of shear stress.

The present invention is directed to a method to determine a rheological property of a fluid. The method includes the step of introducing a flow of fluid in a fluid channel formed in a micro-fluidic device. Further, the method includes the step of measuring a pressure drop of the fluid across a first section of the fluid channel that extends from a first pressure site to a second pressure site utilizing a differential pressure sensor. Further still, the method includes the differential pressure sensor that can be in fluid communication with the first and the second pressure site. Also, the method includes the step of transmitting flow rate data and pressure drop data to a processor. Finally, the method includes the step of calculating a rheological property from the flow rate data and the pressure drop data.

According to a feature of the invention, the method includes the flow rate of the flow that can be determined by introducing the fluid into the fluid channel at an externally controlled flow rate.

According to a feature of the invention, the method includes a flow rate of the flow that can be an uncontrolled flow and measured with a flow rate sensor.

According to a feature of the invention, the method includes the rheological property of the fluid being calculated as the viscosity of the fluid.

According to a feature of the invention, the method includes the micro-fluidic device having a plurality of differential pressure sensors in fluid communication with a plurality of sections of the fluid channel that can be connected in series.

According to a feature of the invention, the method includes each section of the plurality of sections that can be formed with a different cross sectional geometry or length.

According to a feature of the invention, the method includes the micro-fluidic device having a plurality of flow rate sensors formed in the micro-fluidic device and in fluid communication with a plurality of sections of the fluid channel that can be connected in parallel.

According to a feature of the invention, the method includes each section of the plurality of sections that can be formed with a different cross sectional geometry or length.

According to a feature of the invention, the method includes the rheological property that can be calculated from one or a plurality of pairs of flow rate (Q) and pressure drop (Δp) data values.

According to a feature of the invention, the method includes the rheological property that can be calculated from one or a plurality of pairs of flow rate (Q) and pressure drop (Δp) data values.

According to the present of the invention, a micro-fluidic device can be used for measuring one or more rheological properties of a fluid. The micro-fluidic device can include a substrate and at least one cover bonded to a surface of the substrate with a fluid channel formed in at least one of the cover or the substrate. Further, the micro-fluidic device includes a first differential pressure gauge that can have a first differential pressure sensor in fluid communication with both a first pressure site and a second pressure site. Further still, the micro-fluidic device includes the first pressure site and the second pressure site that can be spaced apart by a first section of the fluid channel. Also, the micro-fluidic device includes a data processor communicatively coupled to the first differential pressure sensor, so as to receive data generated by the first differential pressure sensor.

According to a feature of the invention, the first differential pressure sensor includes a first fluid conduit separated from a second fluid conduit by a substrate membrane with the first fluid conduit in fluid communication with the first pressure site and the second fluid conduit in fluid communication with the second pressure site.

According to a feature of the invention, the deflection of the substrate membrane engages a sensor selected from the group consisting of a piezo-resistive sensing element, a capacitor system and an optical system.

According to a feature of the invention, a second differential pressure gauge has a second differential pressure sensor in fluid communication with both a third pressure site and a fourth pressure site, the third pressure site and the fourth pressure site being spaced apart by a second section of the fluid channel where the first section and the second section have different cross sectional geometries or lengths and are disposed in series.

According to a feature of the invention, a first flow sensor is communicatively coupled to the data processor to transmit data that can be formed within the substrate and is in fluid communication with the fluid channel.

According to a feature of the invention, a second differential pressure gauge can have a second differential pressure sensor in fluid communication with both a third pressure site and a fourth pressure site. The third pressure site and the fourth pressure site can be spaced apart by a second section of the fluid channel where the first section and the second section have different cross sectional geometries or lengths and are disposed in series, such that the second differential pressure sensor is communicatively coupled to the data processor.

According to a feature of the invention, the first flow sensor can be a micro electro mechanical system (MEMS) device.

According to a feature of the invention, the first section and a second section of the fluid channel can be disposed in parallel, such that the first section and the second section of the fluid channel have different cross sectional geometries or lengths. Further, a second flow sensor can be communicatively coupled to the data processor to transmit data, and may be in line with the second section of the flow channel and the first flow sensor may be in line with the first section of the flow channel.

According to a feature of the invention, the first differential pressure sensor can be a micro electro mechanical system (MEMS) device.

According to a feature of the invention, the one or more rheological properties of the fluid being measured can be the viscosity of the fluid.

According to the present of the invention, a micro-fluidic device can be used for measuring one or more rheological properties of a fluid. The micro-fluidic device includes a substrate and at least one cover bonded to a surface of the substrate with a fluid channel formed in at least one of the cover, the substrate or a combination of the cover and the substrate. Further, a first absolute pressure gauge can have a first pressure sensor in fluid communication with both a first pressure site and an external pressure. Further still, a second absolute pressure gauge can have a second pressure sensor in fluid communication with both a second pressure site and the external pressure, wherein the first pressure site and the second pressure site are spaced apart by a first section of the fluid channel. Also, at least one flow sensor can be formed in the substrate and in fluid communication with the fluid channel. Further, the first pressure sensor, the second pressure sensor and at least one flow sensor can be communicatively coupled to a data processor to transmit data.

According to a feature of the invention, the first pressure sensor and the second pressure sensor can be micro electro mechanical system (MEMS) devices having respective first and second separate fluid conduits separated from the external pressure by substrate membranes with the first fluid conduit in fluid communication with the first pressure site and the second fluid conduit in fluid communication with the second pressure site.

According to a feature of the invention, a third absolute pressure gauge and a fourth absolute pressure gauge can be in fluid communication with a second section of the fluid channel, wherein the first and the second section of the fluid channel have different cross sectional geometries or lengths and can be disposed in series.

According to a feature of the invention, the two or more flow rate sensors can be formed in the micro-fluidic device and in fluid communication with two or more sections of the fluid channel that can be connected in parallel.

According to a feature of the invention, the one or more rheological properties of the fluid can measured a viscosity of the fluid.

The details of one or more embodiments of the invention are set forth in the accompanying drawings and the description below. Other features, objects and advantages of the invention will be apparent from the description and drawings, and from the claims.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein:

FIGS. 2a and 2b illustrate in cross sectional representation a fluid channel portion of the micro-fluidic sensor according to an aspect of the invention of FIG. 1;

FIG. 3 illustrates in cross sectional representation a differential pressure sensor integrated into the micro-fluidic sensor according to an aspect of the invention of FIG. 1;

FIG. 5 illustrates in cross sectional representation a flow rate sensor integrated into the micro-fluidic sensor according to an aspect of the invention of FIG. 4;

DETAILED DESCRIPTION OF THE PREFERRED EMBODIMENTS

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice. Further, like reference numbers and designations in the various drawings indicated like elements.

The present invention is directed to a micro-fluidic sensor (also referred as a micro-fluidic device) for measuring one or more rheologic properties of a fluid. In a preferred embodiment, the micro-fluidic sensor including a first substrate in which a differential pressure gauge is formed having one side in fluid communication with a first pressure site, and the other side in communication with a second pressure site, the two pressure sites being connected by a fluid channel. The fluid channel may be made in the same substrate as the differential pressure gauge, or it may be made in a different substrate, adjacent and bonded to the first substrate. A signal conduit effectively transmits data generated by the first differential pressure sensor to a data processor.

According to an aspect of, the invention, the measurement of rheological properties of a fluid, such as its viscosity, can be accomplished by having a knowledge of the pressure drop developing in fluid flowing at a known rate through a capillary tube. For example, such a measurement may be performed by either several absolute pressure gauges or one or more differential pressure gauges. In a case where the absolute pressure is high, and the viscous pressure drop along the capillary is small, then a differential pressure gauge will have increased accuracy and precision compared to the case where several absolute pressure gauges are used. In a case where both the viscous pressure drop and the absolute pressure are known and to be of similar magnitude, then either method can be used, the choice being determined may be by other criteria such as ease or cost of fabrication. The flow rate may be either externally controlled or may be measured by using a flow meter.

According to an aspect of the invention, the calculation of viscosity from the pressure drop $\Delta p$ and flow rate Q data for a specific channel geometry and for both Newtonian and non-Newtonian fluids can be performed as described above with particular reference to one of Equations 1, 4, 7, 10, 12 and 14, using the one most appropriate for the geometry and fluid at hand.

Figure 1:
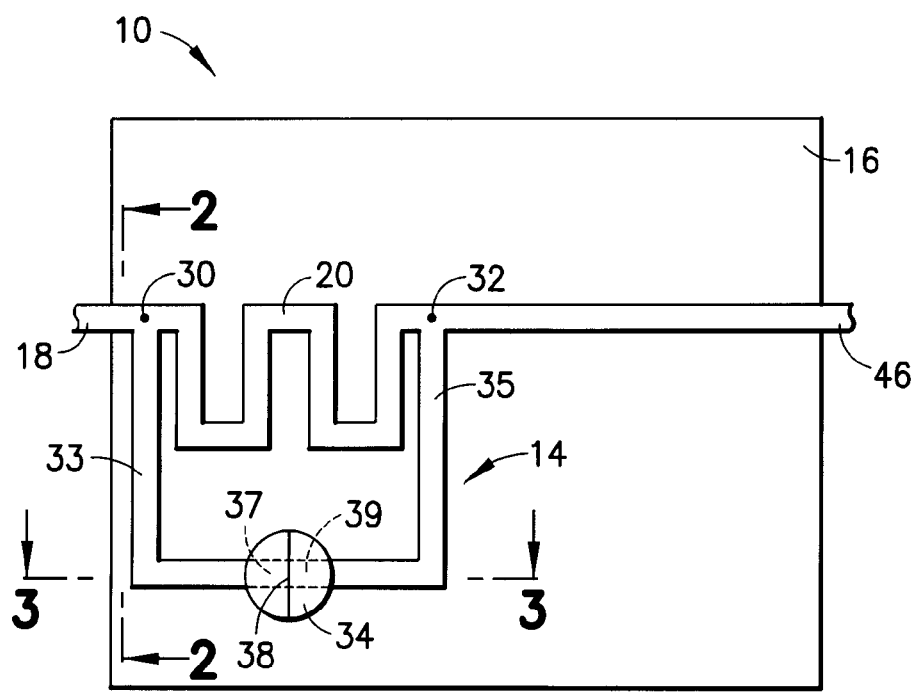
FIG. 1 illustrates according to an embodiment of the invention, a micro-fluidic sensor effective to measure rheological properties of a fluid having either Newtonian or non-Newtonian flow in applications where the flow rate can be externally controlled.

FIG. 1, according to an aspect of the invention, shows in top planar view a micro-fluidic sensor 10 effective for rheological measurements in environments where flow rate can be externally controlled, as may be the case in a lab or up hole environment. The micro-fluidic sensor 10 includes a differential pressure gauge 14 that may be a MEMS device formed on substrate 16. The differential pressure gauge 14 measures a pressure differential as a fluid flows between two points. By utilizing pressure differential data and other data as described below, the micro-fluidic sensor 10 is used to calculate rheological properties of a fluid, such as the absolute viscosity.

Still referring to FIG. 1, the differential pressure gauge 14 includes a fluid channel 20 that extends from a first pressure site 30 to a second pressure site 32. An upstream conduit 33 branches from the first pressure site 30 and a downstream conduit 35 branches from the second pressure site 32. The upstream conduit 33 terminates at an upstream side 37 of a pressure sensor 34 and the downstream conduit 35 terminates at a downstream side 39 of the pressure sensor 34. A substrate membrane 38 separates the upstream side 37 from the downstream side 39. Fluid at the upstream side 37 is at the same pressure as the fluid at the first pressure site 30 and fluid at the downstream side 39 is at the same pressure as the fluid at the second pressure site 32. There is a pressure differential across the substrate membrane 38 equal to the pressure differential over the length of the fluid channel 20. Substrate membrane 38 flexes as a result of this pressure differential and by measuring the amount of flex, the pressure differential is determined.

According to an aspect of the invention, the flow rate can be externally controlled by a micro-syringe or controlled flow pump so as to control a flow of the fluid into the micro-fluidic sensor, such as in a lab or up hole applications. Hence, knowledge of the flow rate and the pressure drop along a well defined channel suffices to accurately measure absolute viscosity. For a Newtonian fluid, the above relation holds irrespective of the flow rate or equivalently the shear stress at the channel wall surface.

Still referring to FIG. 1, according to an aspect of the invention, the fluid inlet 18 introduces a fluid into a fluid channel 20 with known dimensions and of known cross-sectional geometry. To facilitate measurements of non-Newtonian flows, circular or slit-like cross-sections are preferred. When the geometry of the cross-section is slit-like, for example when the aspect ratio exceeds about 10:1, the edge effects are negligible and an aspect ratio in excess of 10:1 may be preferred for enhanced accuracy. For ease of manufacture, a rectangular cross-section with aspect ratio close to unity may be preferred.

FIGS. 2a and 2b according to an aspect of the invention show cross-sections of the micro-fluidic sensor 10 along line 2-2 of FIG. 1. The fluid channel 20 may be formed by any method that is effective to achieve a consistent geometry along the length of the channel between two pressure sites on opposing sides of a pressure sensor. It is possible according to an aspect of the invention, as represented in FIG. 2a, the substrate 16 is made of a semiconductor material such as silicon, Silicon on Insulator (SOI), glass or gallium arsenide, and the fluid channel 20 is partly etched into it by a dry plasma, ultrasonic, or wet chemical etching method. A top cover 26 and a bottom cover 28 can be made of several types of glass (Pyrex, Borofloat), ceramic material or silicon, are then bonded to the substrate 16. When the substrate 16 is a silicon based material and the covers 26, 28 are made of glass or silicon, anodic, direct silicon or eutectic bonding methods may be utilized for bonding the cover to the substrates. If both the substrate 16 and the covers 26, 28 are glass, direct (diffusion) bonding can be performed. The assembled structure has a fluid channel 20 of controlled geometry.

FIG. 2b according to an aspect of the invention shows the fluid channel 20 that may be formed in one of the covers 28 and be disposed adjacent the substrate 16.

It is possible the instant invention can include miniature devices that may be manufactured by using fabrication techniques common to the integrated circuit and MEMS technologies. These involve fabrication processes for patterning and machining materials like polymeric photoresists, silicon, glass, metal films, silicon oxide, nitride, and the like which allow fabrication of very small mechanical devices.

FIG. 3 according to an aspect of the invention shows the operation of the pressure sensor 34 component of the differential pressure gauge illustrated in cross sectional representation, which is viewed along line 3-3 of FIG. 1. The fluid channel, upstream conduit 33 and downstream conduit 35 may be manufactured in the substrate 16 or in either of the covers 26, 28. Any suitable fabrication method may be utilized, such as sand blasting, ultrasonic fabrication, dry plasma etching, chemical wet etching, laser ablation, etc. In one possible implementation, the upstream conduit 33 is partially formed in a first side of substrate 16 and partially in top cover 26. A backside trench 41 is then formed in an opposing second side of the substrate 16. Material removal for the backside trench is stopped short of piercing through the substrate 16, such that a thin substrate membrane 38 remains. The downstream conduit 35 is partially formed by the backside trench 41 and partially in the back cover 28.

Still referring to FIG. 3, according to an aspect of the invention, the substrate membrane 38 is sufficiently thin to deflect under the pressure difference between fluid in the upstream conduit 33 and fluid in the downstream conduit 35. Typically, the substrate membrane 38 has a thickness on the order of one to hundreds of micrometers thick. The amount of deflection of the substrate membrane 38 is proportional to the pressure difference. The deflection may be measured by any effective means, such as a piezo-resistive sensing element 40 deposited on the substrate membrane 38, a capacitor system or an optical system. The piezo-resistive sensing element 40 is deposited on top of an insulator layer 42 coating a surface portion of the substrate membrane 38 and is defined by lithography and etching. When excited using an external voltage source, the piezo-resistive sensing element 40 outputs a voltage proportional to the amount of deflection and therefore proportional to the fluid pressure difference between the fluid at the first pressure site and the fluid at the second pressure site. Since the pressure difference, which tends to be rather small, is not affected by the ambient pressure, which may vary over a wide range of values, the differential pressure gauge is effective for a wide range of fluid pressures. Metallized circuit traces 44 may be utilized to conduct the voltage output of the piezo-resistive sensing element 40 to a surface of the substrate 16. The circuit traces 44 may then be coupled to a volt meter, an acquisition board, an oscilloscope, a dedicated electronic circuit, other voltage measuring device or a processor to facilitate calculating a rheological property from the flow rate data and the pressure drop data.

According to an aspect of the invention, by increasing the distance between the first pressure site 30 and the second pressure site 32 will result in increasing the pressure drop and therefore the sensitivity of the measurement. Fluid channel 20 may have a serpentine configuration as illustrated in FIG. 1 or any other suitable shape to enhance length. After traversing the second pressure site 32, the fluid exits the micro-fluidic sensor 10 at fluid outlet 46.

Figure 4:
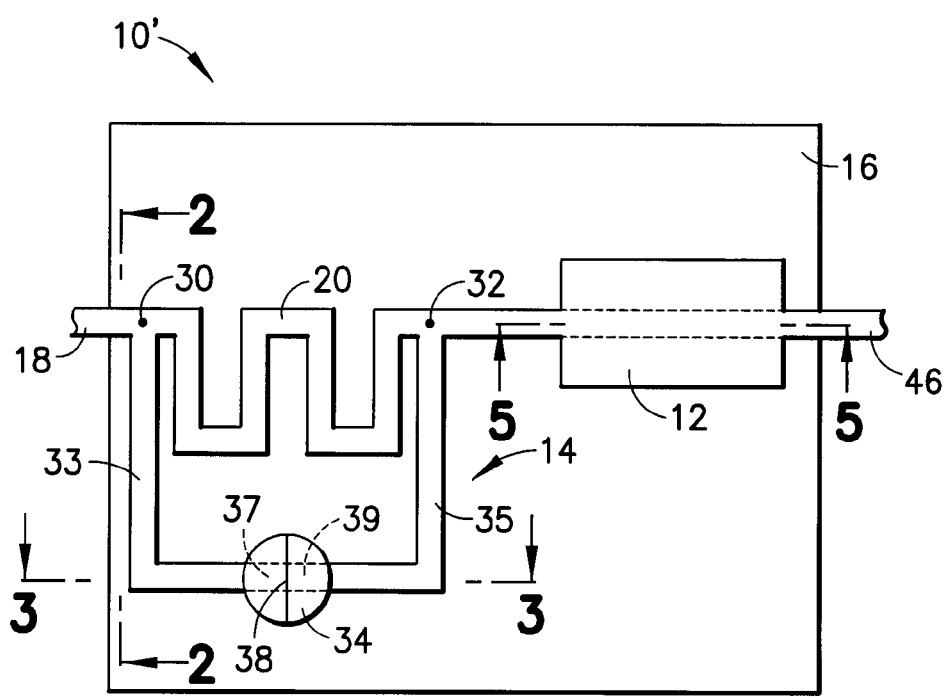
FIG. 4 illustrates according to an aspect of the invention a micro-fluidic sensor effective to measure rheological properties of a fluid having Newtonian flow in applications where flow rate cannot be externally controlled.

FIG. 4 according to an aspect of the invention, shows that many applications, such as down hole oilfield applications (for example), may not be practical to externally control the flow. In particular, FIG. 4 illustrates a micro-fluidic sensor 10' effective for applications where the flow is not externally controlled. This micro-fluidic sensor 10' includes a flow rate sensor 12. The flow rate sensor may be a MEMS device formed into substrate 16. An exemplary MEMS flow rate sensor 12 is illustrated in FIG. 5 as viewed along cross-sectional line 5-5 of FIG. 4. A tracer emitter 48 emits a tracer (typically in the form of a heat pulse) into the fluid flowing through fluid channel 20. A first tracer detector 50 and, potentially, a second tracer detector 52 are utilized to detect the tracer signal and to calculate the time of travel of the tracer from tracer emitter 48. The tracer emitter 48 as well as the tracer detectors 50, 52, may be implemented on a wall of the fluid channel 20, or they may extend as bridges across the fluid channel, as represented in FIG. 5.

Typically, the tracer is emitted as pulses at precisely timed intervals. However, according to an aspect of the invention, the tracer may be emitted in the form of a stochastic or pseudo-random sequence, in which case the time of flight may be determined by performing cross correlation between the emitted tracer signal and the signals detected by tracer detectors 50, 52. Multiple data points, including: (1) the time to traverse from tracer emitter 48 to the first tracer detector 50; (2) the time to traverse from the tracer emitter 48 to the second tracer detector 52; and (3) the time to traverse from the first tracer detector 50 to the second tracer detector 52 may be utilized to accurately calculate flow rate.

According to an aspect of the invention, one example of a MEMS flow rate sensor 12 may have a suspended bridge as the tracer emitter 48. Such that by applying a voltage via resistive circuit trace 44 can cause the temperature of the tracer emitter 48 to increase by a known amount. Wherein a thermal pulse is conducted by the fluid through the fluid channel 20. The time for the thermal pulse to reach the first suspended tracer detector bridge 50 and the second suspended tracer detector bridge 52 may be determined by utilizing resistive temperature detectors 44', 44" (RTD) or thermocouples disposed on the suspended tracer detector bridges 50, 52. Resistive circuit traces 44', 44" are effectively used as RTDs to transmit tracer signals from the suspended tracer detector bridges 50, 52 to an external measuring circuit, such as an oscilloscope, a voltmeter, an acquisition board, a dedicated electronic circuit or other voltage measuring device.

Figure 6:
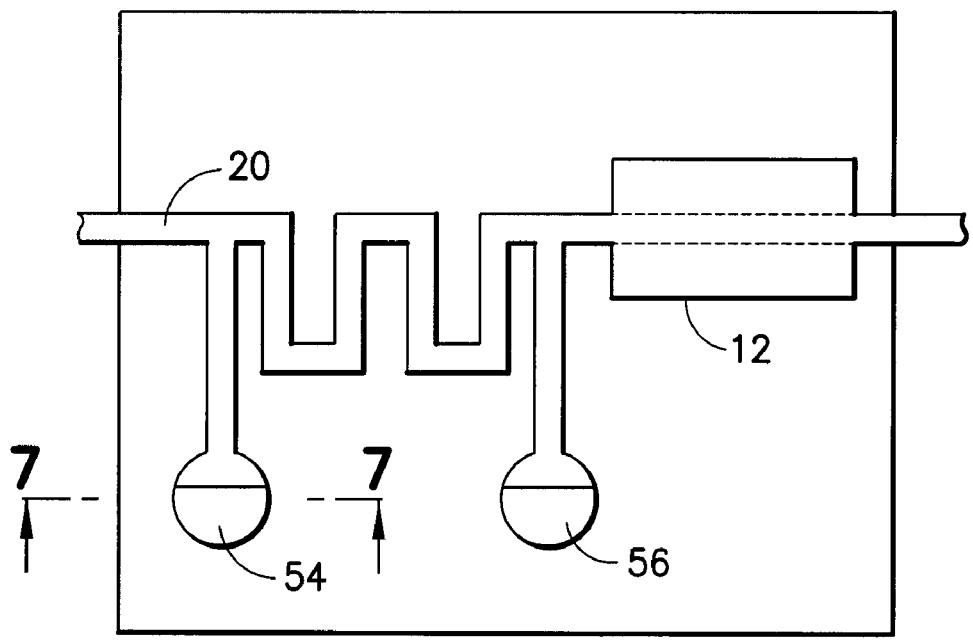
FIG. 6 illustrates according to an aspect of the invention, a micro-fluidic sensor effective to measure rheological properties of a fluid utilizing absolute pressure gauges.

FIG. 6 according to another embodiment of the invention, shows utilizing two or more absolute pressure gauges 54, 56 spaced apart along fluid channel 20. The pressure drop along the fluid channel 20 is obtained by subtracting the responses of the absolute pressure gauges, and the flow rate is measured using flow rate sensor 12. Similar embodiments as describe herein for differential pressure gauges may be applied to absolute pressure gauges, such as channels disposed in parallel or in series.

Figure 7:
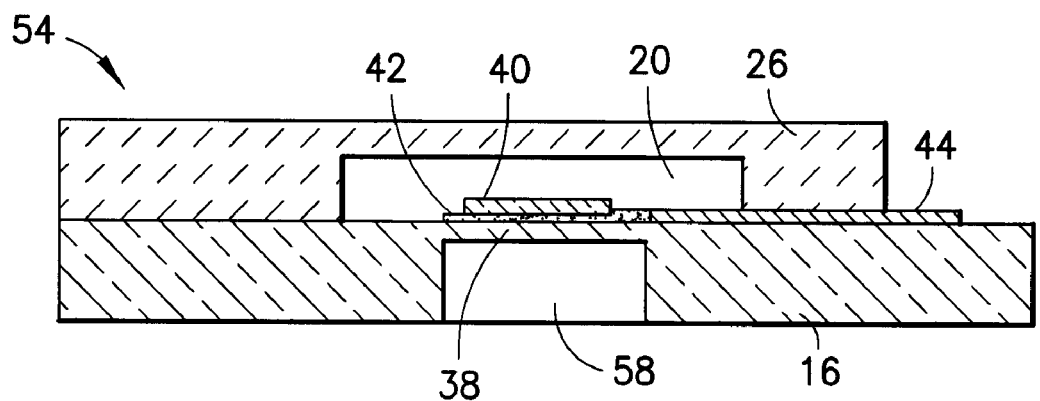
FIG. 7 illustrates in cross sectional representation an absolute pressure gauge according to an aspect of the invention of FIG. 6.

Still referring to FIG. 6, according to an aspect of the invention, the fabrication of the fluid channel 20 and flow rate sensor is identical to that described above. The fabrication of the absolute pressure gauge is 54 similar, except as shown in FIG. 7, the back side of the substrate membrane 38 is exposed to an external pressure on the outside of the chip via open channel 58. The external pressure may be at atmospheric pressure or at some other outside pressure that is common between the absolute pressure gauges. Since all absolute pressure gauges see this same external pressure, when their responses are subtracted, a measure of the pressure drop along the fluid channel is obtained.

Since the micro-fluidic sensor 10' illustrated in FIG. 4 is effective to determine all variables necessary to calculate the absolute viscosity, absolute viscosity may be determined in the field or in situ and does not require external devices such as control flow pumps.

For a non-Newtonian, but incompressible, fluid flowing in a cylindrical tube, the shear stress rate at the wall needs to be calculated using the Rabinowitsch equation:

$$\dot{\gamma}_W = \dot{\gamma}_{WN}\left(\frac{3}{4} + \frac{1}{4}\frac{\partial \log(\dot{\gamma}_{WN})}{\partial \log(W)}\right) \quad (5)$$

Variants of this equation for other cross-sectional geometries exist as described above.

The user controllable parameters to determine $\dot{\gamma}_{WN}$ and W are the flow rate, Q, and the pressure drop, $\Delta P$. Once $\dot{\gamma}_{WN}$ and W are inferred from several measured pairs of values (Q, $\Delta P$), $\dot{\gamma}_W$ is calculated from the Rabinowitsch equation. The absolute viscosity, $\eta$, can then be calculated from the $\eta = W/\dot{\gamma}_W$. It is now possible to measure the shear rate dependence of the viscosity in a matter akin to a true rheometer.

According to an aspect of the invention, in some environments, such as a lab or an up hole environment, it may be possible to control the flow rate precisely with a syringe pump. By sweeping the flow rate across multiple ranges, one obtains the range of shear stresses essentially varying $\dot{\gamma}_{WN}$. However, an external pump may not be practical for some applications, notably in a down hole implementation. For these applications, alternative embodiments as illustrated in FIGS. 4, 6, 8 and 9 may be utilized.

Figure 8:
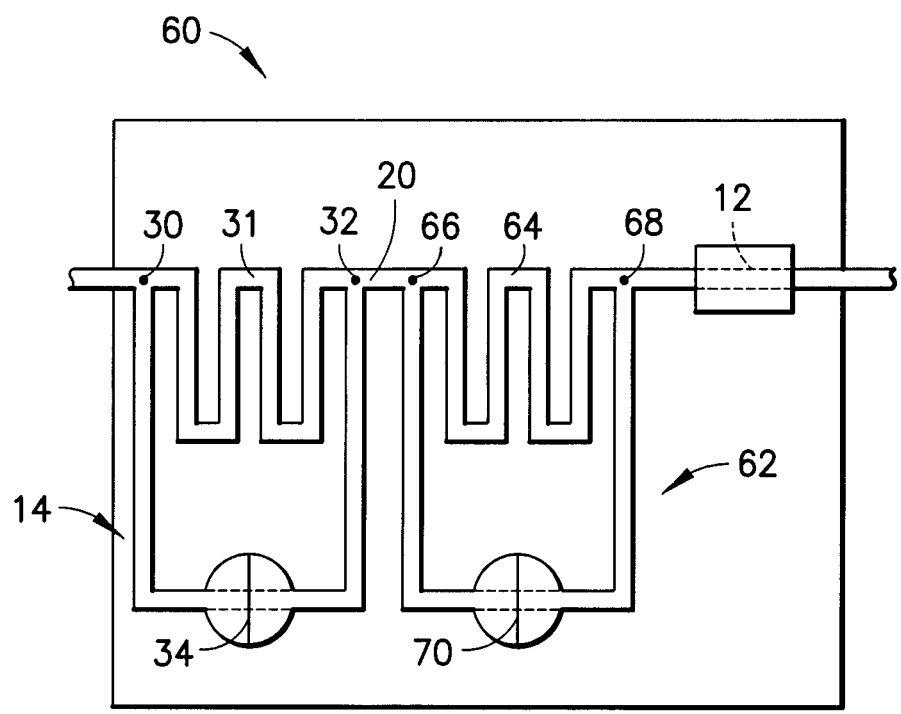
FIG. 8 illustrates according to an aspect of the invention, a micro-fluidic sensor effective to measure rheological properties of a fluid having either Newtonian or non-Newtonian flow.

FIG. 8 according to an aspect of the invention, shows that the micro-fluidic sensor 60 includes a first differential pressure gauge 14 and a second differential pressure gauge 62. The first differential pressure gauge 14 includes first pressure sensor 34 that measures the pressure difference along a first section 31 of the fluid channel 20. The second differential pressure gauge 62 includes a second pressure sensor 70 that measures the pressure difference along a second section 64 of the fluid channel 20. The cross-sectional geometry and/or length of the first section 31 is typically different from the cross-sectional geometry and/or length of the second section 64, leading to different wall shear rates. The first pressure sensor 34 is used to determine a first pressure drop between first and second pressure sites 30, 32. The second differential pressure sensor 70 is used to measure the pressure drop between third pressure site 66 and fourth pressure site 68. The pressure difference is accurately measured in each section 31, 64 and each pressure sensor 34, 70 output is then used to calculate a viscosity at a different shear rate. The micro-fluidic sensor 60 is not limited to only two differential pressure gauges 14, 62 and two fluid channel sections 31, 64 of differing cross-sectional geometry and/or length; arbitrary numbers of differential pressure gauges and fluid channel sections may be added as needed to improve precision and/or operating range of the micro-fluidic sensor 60.

According to an aspect of the invention, for example in non Newtonian fluids, the pressure measured using a distant pressure gauge may be different than the pressure that would be measured by a pressure gauge placed directly in the flow. This discrepancy is termed "hole pressure error" and arises from normal stress differences present in the flow of non-Newtonian solutions. For differential measurement between two regions of identical geometry (such as first and second pressure sites 30, 32 or third and fourth pressure sites 66, 68), the hole pressure error exactly cancels and the measurement will be unaffected. As a result, for the micro-fluidic sensor 60, the hole pressure error is unimportant for measuring shear stress dependent viscosity. If, however, a differential measurement is taken between two regions with different wall shear rates, there will be a measurable discrepancy that can be related to the normal stress differences in the flow.

Figure 9:
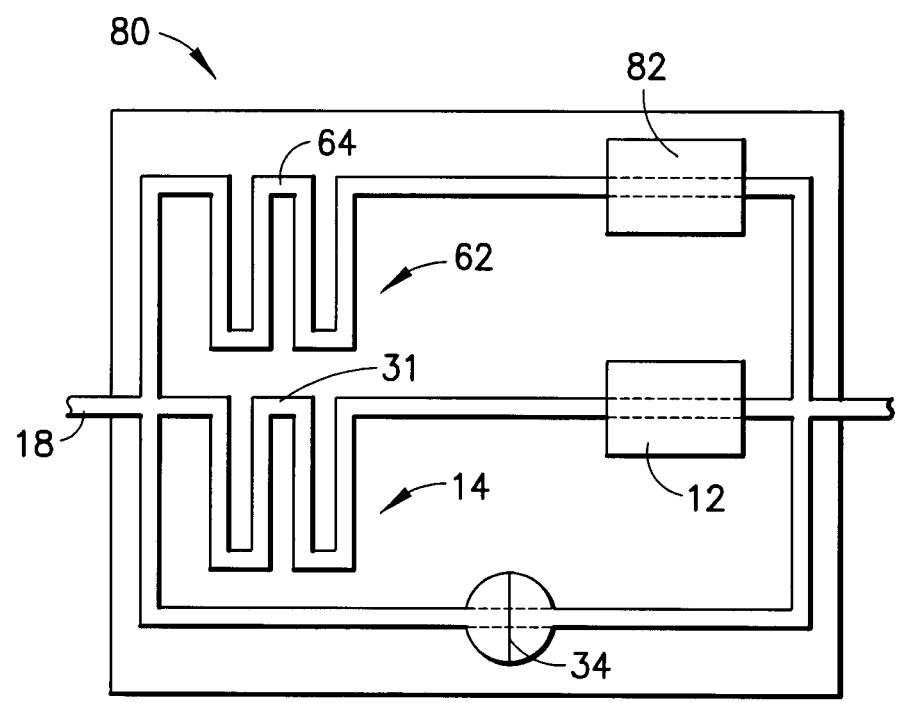
FIG. 9 is another embodiment of the invention illustrating a micro-fluidic sensor that is effective to measure Theological properties of a fluid having either Newtonian or non-Newtonian flow.

FIG. 9 according to another embodiment of the invention, shows a micro-fluidic sensor 80 having the first fluid channel section 31 and the second fluid channel section 64 control parallel flow channels. Wherein, the fluid channel sections 31, 64 can be made with different cross-sectional geometries, and thus the fluid passing through them will be exposed to different wall shear rates. A single differential pressure sensor 34 measures the pressure drop across both channel sections. Separate flow rate sensors 12, 82 determine the different flow rates in each fluid channel section 31, 64. Similar to the preceding embodiment, additional channel sections may be added in parallel.

Figure 10:
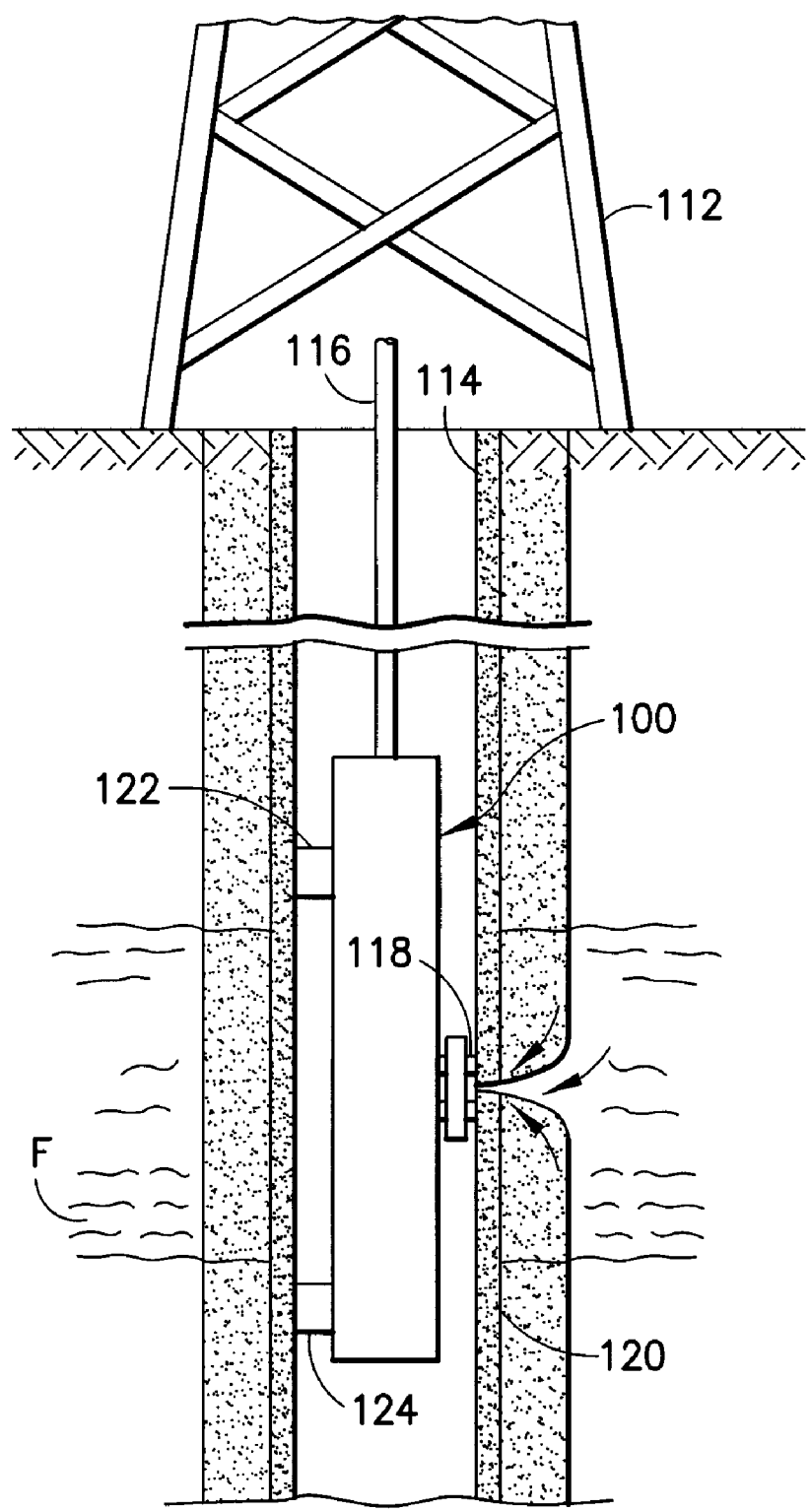
FIG. 10 illustrates according to an aspect of the invention, a down hole tool that may include a micro-fluidic sensor as disclosed herein.

Referring to FIG. 10, according to an aspect of the invention, it is possible for the micro-fluidic device to be incorporated into a down hole oil field tool. For example, the down hole tool may include: a logging while drilling (LWD) tool; production logging (PL) tool; a wireline open hole logging tool; a well testing tool or assembly; or a tool performing different well services; or it may be part of a permanent monitoring station. FIG. 10 represents an example showing a wireline open hole tool 100 suspended from a rig 112 by a wireline cable 116 into a well bore 114. The down hole tool 100 represented in FIG. 10 includes a Modular Dynamic Tester (MDT™ tool) (MDT is a trademark of Schlumberger Ltd., Houston, Tex.) enabling sampling during wire line logging operations. The illustrative down hole tool 100 is a wire line tool deployed from the rig 112 into the well bore 114 via a wire line cable 116 and positioned adjacent to a formation, "F". The down hole tool 100 is provided with a probe 118 adapted to seal with a wall 120 of the well bore 114 and draw fluid from the formation, "F," into the down hole tool 100 as depicted by the arrows. Backup pistons 122 and 124 assist in pushing the probe 118 of the down hole tool 100 against the well bore wall 120.

A micro-fluidic sensor is supported within the down hole tool 100 which is positioned at a depth of interest in the well bore 114. Referring back to FIG. 4, a substream of the reservoir fluid flows through fluid inlet 18 from formation F into the tool, from where it is directed into a micro-fluidic sensor 10'. The flow velocity is measured by flow rate sensor 12, so is not necessary to control the flow rate at the fluid inlet. The fluid flows through the fluid channel 20 and a pressure differential is measured by the pressure sensor 34. The pressure drop and the flow rate may be transmitted by a suitable method such as electrical or optical signals to a processor that then calculates absolute viscosity.

According to an aspect of the invention, it is possible for the micro-fluidic sensors to be used in an up hole application. For example, the micro-fluidic sensors may be incorporated in the preparation of fluids to prop open fracture surfaces of a well hole at a desired depth. A fluid with very specific rheological properties is needed to help sweep proppants into formation cracks. The fluid is controlled on-site by mixing local water with chemicals (worm-like micelles). As the local water content (salts, contaminants) varies dramatically worldwide, the resulting viscosity of the suspension tends to vary as well. By having an on-site measurement available, quality control is available for the field engineer. The field engineer prepares an aqueous mixture and then flows a sample into the micro-fluidic sensor 10' via inlet 18. Absolute viscosity is then measured and if the absolute viscosity is within a target range, the mixture may then be injected into a borehole at a desired depth.

Application of the micro-fluidic sensors of the invention will be better understood by the Example that follows:

EXAMPLE

Figure 11:
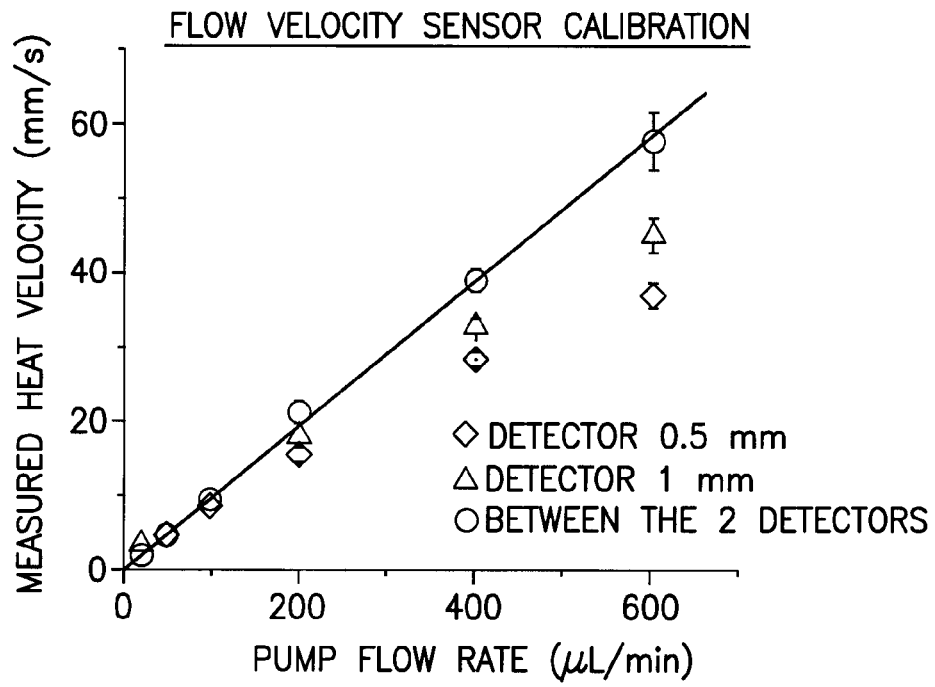
FIG. 11 graphically illustrates according to an aspect of the invention, a relationship between flow rate and fluid velocity, as measured by a thermal tracer flow meter, in a fluid channel.

FIG. 11 graphically illustrates one embodiment of the flow rate sensor 12 of FIG. 5. A small volume of hexadecane was introduced into the flow rate sensor at a pump flow rate, in microliters per minute, determined by an external pump. Thermal pulses were generated by tracer emitter 48 and the time for the thermal pulse to reach first tracer detector 50 (represented by diamonds) and second tracer detector 52 (represented by triangles), measured as heat velocity in millimeters per second. The time for the thermal pulse to traverse the distance from the first tracer detector 50 to the second tracer detector 52 was also plotted in FIG. 9 (represented by circles) and is a straight line. This indicated that if the flow rate sensor 12 measured the heat velocity, the flow rate of a liquid may be calculated accurately. It was therefore not necessary to know a-priori the flow rate of a test fluid demonstrating that the micro-fluidic sensors described herein are effective for down hole applications.

Figure 12:
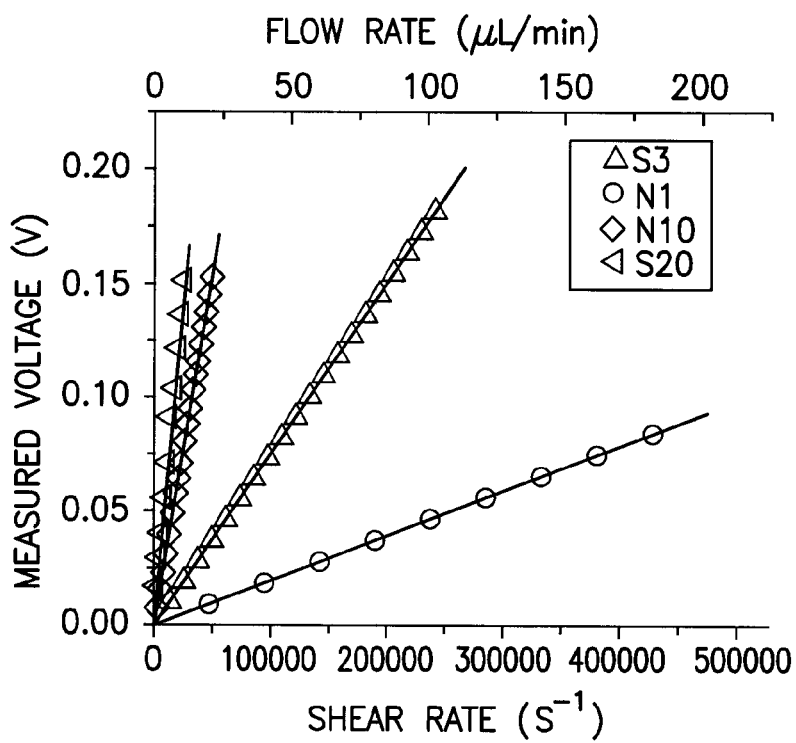
FIG. 12 graphically illustrates according to an aspect of the invention, a relationship between flow rate, or, equivalently, wall shear rate, and pressure differential for several Newtonian fluids.

FIG. 12 demonstrates that at a constant viscosity there was a linear relationship between flow rate, measured in microliters per minute, and the output of the differential pressure gauge, $\Delta P$, measured in Volts. Several Newtonian control viscosity fluids were used as references. These fluids are available from Cannon Instrument Company of State College, Pa., and have the following room temperature (20° C.) values in centipoises:

| Fluid Designation | Room Temperature Nominal Viscosity |
|---|---|
| N1 | 0.93 cP |
| S3 | 3.9 cP |
| N10 | 21 cP |
| S20 | 37 cP |

Figure 13:
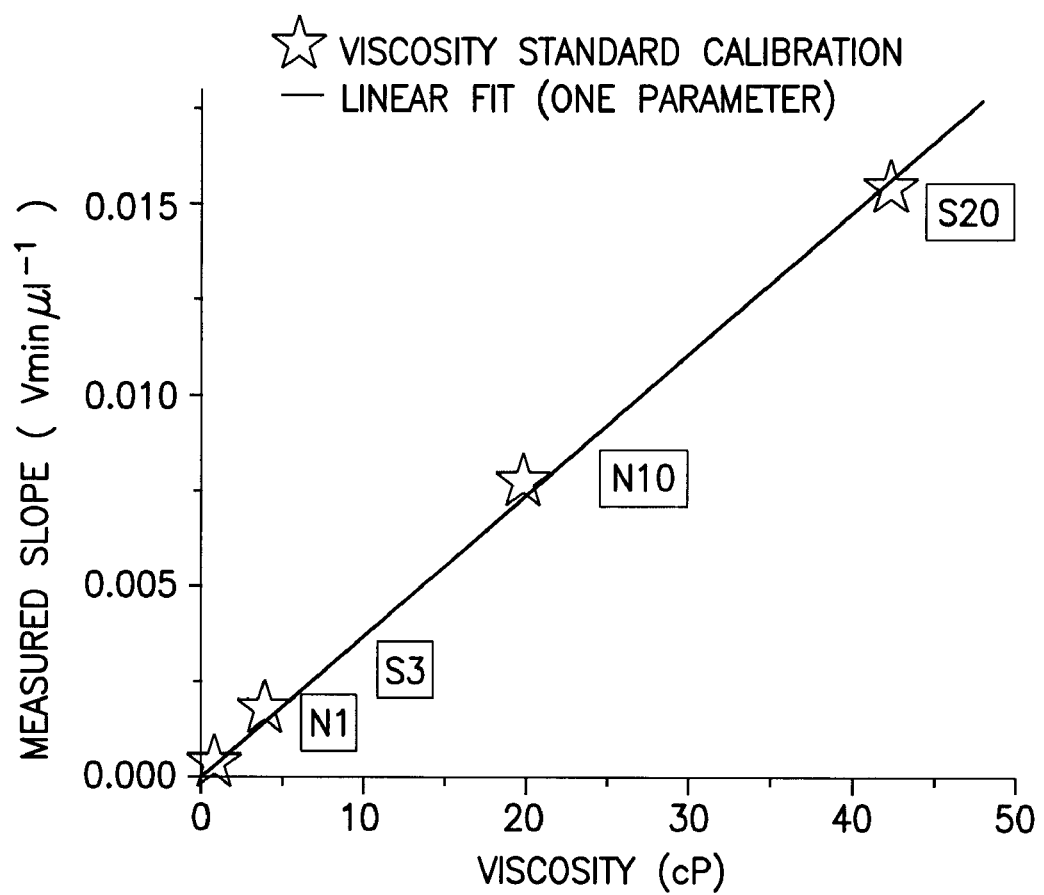
FIG. 13 graphically illustrates -according to an aspect of the invention, the linear relationship between measured ratio of pressure drop to flow rate, as measured using the principles described herein, and the absolute viscosity of the test fluids used.

From FIG. 12, it is seen that the viscosity for a Newtonian flow is obtained by dividing the change in pressure by the flow rate, $\Delta P/Q$ and, from FIG. 13, it is seen that the slopes of the linear fits from FIG. 12, vs actual viscosity of the calibration standards form a linear relationship. The linear dependence shows that the sensor can actually measure accurately non-Newtonian fluid viscosities, provided prior calibration using at least one viscosity standard.

It is noted that the foregoing examples have been provided merely for the purpose of explanation and are in no way to be construed as limiting of the present invention. While the present invention has been described with reference to an exemplary embodiment, it is understood that the words, which have been used herein, are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A method to determine a rheological property of a fluid, the method comprising:
   introducing a flow of said fluid in a fluid channel formed in a micro-fluidic device;
   measuring a pressure drop of said fluid across a first section of said fluid channel that extends from a first pressure site to a second pressure site utilizing a differential pressure sensor, wherein said differential pressure sensor is in fluid communication with said first and said second pressure site;
   transmitting flow rate data and pressure drop data to a processor so as to calculate a time of flight flow rate measurement wherein the calculated time of flight flow rate measurement data is stored as calculated data; and
   calculating the rheological property from said flow rate data, said pressure drop data and said calculated data.

2. The method of claim 1, wherein the flow rate of said flow is determined by utilizing a flow measurement device within the micro-fluidic device which has the differential pressure sensor.

3. The method of claim 1, wherein the flow rate of said flow is an uncontrolled flow and is measured with a flow rate sensor.

4. The method of claim 1, wherein said rheological property of said fluid being calculated is a viscosity of said fluid.

5. The method of claim 1, wherein said micro-fluidic device includes a plurality of differential pressure sensors in fluid communication with a plurality of sections of said fluid channel.

6. The method of claim 5, wherein each section of said plurality of sections is formed with a different cross sectional geometry or length.

7. The method of claim 3, wherein said micro-fluidic device includes a plurality of flow rate sensors formed in said micro-fluidic device and in fluid communication with a plurality of sections of said fluid channel that are connected in parallel or series.

8. The method of claim 7, wherein each section of said plurality of sections is formed with a different cross sectional geometry or length.

9. The method of claim 6, wherein said rheological property is calculated from one or a plurality of pairs of flow rate (Q) and pressure drop ($\Delta p$) data values and the calculated data or some combination thereof.

10. The method of claim 8, wherein said rheological property is calculated from one or a plurality of pairs of flow rate (Q) and pressure drop ($\Delta p$) data values.

11. A micro-fluidic device for measuring one or more rheological properties of a fluid, the micro-fluidic device comprising:
a substrate;
at least one cover bonded to a surface of said substrate with a fluid channel formed in at least one of said cover or said substrate;
a first differential pressure gauge having a first differential pressure sensor in fluid communication with both a first pressure site and a second pressure site, said first pressure site and said second pressure site spaced apart by a first section of said fluid channel;
wherein said first differential pressure sensor includes a first fluid conduit separated from a second fluid conduit by a substrate membrane with said first fluid conduit in fluid communication with said first pressure site and said second fluid conduit in fluid communication with said second pressure site; and
a data processor communicatively coupled to said first differential pressure sensor, so as to receive data generated by said first differential pressure sensor.

12. The micro-fluidic device of claim 11, wherein deflection of said substrate membrane engages a sensor selected from the group consisting of a piezo-resistive sensing element, a capacitor system or an optical system.

13. The micro-fluidic device of claim 11, wherein a second differential pressure gauge has a second differential pressure sensor in fluid communication with both a third pressure site and a fourth pressure site, said third pressure site and said fourth pressure site being spaced apart by a second section of said fluid channel where said first section and said second section have different cross sectional geometries or lengths and are disposed in series.

14. The micro-fluidic device of claim 11, wherein a first flow sensor is communicatively coupled to said data processor to transmit data is formed within said substrate and is in fluid communication with said fluid channel.

15. The micro-fluidic device of claim 14, wherein a second differential pressure gauge has a second differential pressure sensor in fluid communication with both a third pressure site and a fourth pressure site, said third pressure site and said fourth pressure site spaced apart by a second section of said fluid channel where said first section and said second section have different cross sectional geometries or lengths and are disposed in series, such that said second differential pressure sensor is communicatively coupled to said data processor.

16. The micro-fluidic device of claim 14, wherein said first flow sensor is a micro electro mechanical system (MEMS) device.

17. The micro-fluidic device of claim 14, wherein said first section and a second section of said fluid channel are disposed in parallel, such that said first section and said second section of said fluid channel have different cross sectional geometries or lengths;
a second flow sensor is communicatively coupled to said data processor to transmit data, and is in line with said second section of said flow channel and said first flow sensor is in line with said first section of said flow channel.

18. The micro-fluidic device of claim 11, wherein said first differential pressure sensor is a micro electro mechanical system (MEMS) device.

19. The micro-fluidic device of claim 11, wherein said one or more rheological properties of said fluid being measured is a viscosity of said fluid.

20. A micro-fluidic device for measuring one or more rheological properties of a fluid, the micro-fluidic device comprising:
a substrate;
at least one cover bonded to a surface of said substrate with a fluid channel formed in at least one of said cover, said substrate or a combination of said cover and said substrate;
a first absolute pressure gauge having a first pressure sensor in fluid communication with both a first pressure site and an external pressure;
a second absolute pressure gauge having a second pressure sensor in fluid communication with both a second pressure site and said external pressure, wherein said first pressure site and said second pressure site are spaced apart by a first section of said fluid channel;
wherein said first pressure sensor and said second pressure sensor are micro electro mechanical system (MEMS) devices;
at least one flow sensor formed in said substrate and in fluid communication with said fluid channel; and
wherein said first pressure sensor, said second pressure sensor and said at least one flow sensor are communicatively coupled to a data processor to transmit data.

21. The micro-fluidic device of claim 20, wherein said first pressure sensor and said second pressure sensor are sensors having respective first and second separate fluid conduits separated from said external pressure by substrate membranes with said first fluid conduit in fluid communication with said first pressure site and said second fluid conduit in fluid communication with said second pressure site.

22. The micro-fluidic device of claim 20, wherein a third absolute pressure gauge and a fourth absolute pressure gauge are in fluid communication with a second section of said fluid channel, wherein said first and said second section of said fluid channel have different cross sectional geometries or lengths and are disposed in series.

23. The micro-fluidic device of claim 20, wherein two or more flow rate sensors are formed in said micro-fluidic device and in fluid communication with two or more sections of said fluid channel that are connected in parallel.

24. The micro-fluidic device of claim 20, wherein said one or more rheological properties of said fluid being measured is a viscosity of said fluid.

25. A micro-fluidic device for measuring at least one rheological property of a fluid, the micro-fluidic device comprising:
a substrate;
at least one cover bonded to a surface of said substrate with a fluid channel formed in at least one of said cover or said substrate;
at least one differential pressure gauge having a first differential pressure sensor in fluid communication with both a first pressure site and a second pressure site, said first pressure site and said second pressure site spaced apart by a first section of said fluid channel;

a flow measurement device in fluid communication with at least a portion of the fluid channel that is similarly structured and arranged in the micro-fluidic device as the at least one differential pressure gauge, wherein the flow measurement device is used to determine a flow rate of the fluid; and a data processor communicatively coupled to said first differential pressure sensor and the flow measurement device, so as to receive data generated by said first differential pressure sensor and the flow measurement device.

* * * * *